United States Patent [19]

Kenyon et al.

[11] Patent Number: 4,723,552
[45] Date of Patent: Feb. 9, 1988

[54] TRANSCUTANEOUS ELECTRICAL NERVE STIMULATION DEVICE

[75] Inventors: Keith E. Kenyon, Van Nuys; Thomas F. Conmy, Canoga Park; Fred L. Pedersen, Oxnard, all of Calif.

[73] Assignee: James Heaney, Huntington Beach, Calif.

[21] Appl. No.: 894,729

[22] Filed: Aug. 8, 1986

Related U.S. Application Data

[63] Continuation of Ser. No. 616,610, Jun. 4, 1984, abandoned, which is a continuation of Ser. No. 243,892, Mar. 16, 1981, abandoned.

[51] Int. Cl.⁴ .................................................. A61N 1/36
[52] U.S. Cl. ...................................... 128/421; 128/422
[58] Field of Search .......... 128/419 R, 420 A, 420 R, 128/421-422, 423 A, 423 W

[56] References Cited

U.S. PATENT DOCUMENTS

| 2,350,797 | 6/1944 | Morland et al. | 128/421 |
|---|---|---|---|
| 2,375,575 | 5/1945 | Morland et al. | 128/421 |
| 2,532,788 | 12/1950 | Sarnoff | 128/421 |
| 3,204,637 | 9/1965 | Frank et al. | 128/423 |
| 3,797,500 | 3/1974 | Porter | 128/422 |
| 3,946,745 | 3/1976 | Hsiang-Lai et al. | 128/421 |
| 4,057,069 | 11/1977 | Dorffer et al. | 128/421 |
| 4,157,087 | 6/1979 | Miller et al. | 128/423 R |
| 4,324,253 | 4/1982 | Greene et al. | 128/421 |

FOREIGN PATENT DOCUMENTS 0644459  1/1979  U.S.S.R. .............................. 128/421

Primary Examiner—Edward M. Coven
Assistant Examiner—Angela D. Sykes
Attorney, Agent, or Firm—Blakely, Sokoloff, Taylor & Zafman

[57] ABSTRACT

By generating and applying topically, to a patient suffering pain in the areas in which the patient is experiencing pain, a train of electrical pulses having a stimulation region comprising contiguous, alternately positive and negative triangular pulses followed by a rest region of substantially constant amplitude, which may be zero, the time duration of the rest region being approximately 10 to 15 miliseconds, said stimulation region having a duration of from 2 to 20 miliseconds, optimal pain relieving effects are realized.

1 Claim, 2 Drawing Figures

TRANSCUTANEOUS ELECTRICAL NERVE STIMULATION DEVICE

This is a continuation of application Ser. No. 616,610, filed June 4, 1984, now abandoned, which is a continuation of application Ser. No. 243,892, filed Mar. 16, 1981, now abandoned.

BACKGROUND OF THE INVENTION

1. Field of the Invention

This invention relates to electrical pain-relieving devices and methods and, more particularly, to such devices and methods relying upon transcutaneous nerve stimulation.

2. Prior Art

Prior to 1968, transcutaneous electrical nerve stimulation (TENS) was considered "pseudoscientific" in medical terms. By 1968 TENS therapy had left the realm of pseudoscientific medicine and entered into the realm of a legitimate medical practice with full approval by orthodox medical practitioners. At that time the waveform used by manufacturers of TENS units comprised faradic (sine wave) pulses or galvanic (variants of square wave) pulses. Thereafter, the use of triangular pulses and spikes began. Spikes could be produced simply by means of RC circuits. Triangular pulses were not so easily achieved and required much more complicated circuits but triangular pulses were of far greater benefit to the patient in relieving pain. Triangular pulses also had much greater sedative effect than any of the more simply produced waveforms. The improvement realized by going from other waveforms to a triangular waveform suggested to these inventors the possibility of further improvement by optimizing the way in which triangular waveforms were constituted.

Therefore, it is an object of this invention to overcome the shortcomings of prior TENS devices and methods.

It is a further object of this invention to provide apparatus and a method for producing optimum therapeutic effects from transcutaneous electrical nerve stimulation.

SUMMARY OF THE INVENTION

Stated succinctly, a device and method are provided by which a train of electrical pulses is generated having a stimulation region comprising contiguous, alternately positive and negative triangular pulses followed by a rest region of substantially constant amplitude, which may be zero, the time duration of the rest region being at least equal to ½ the time duration of said stimulation region, said stimulation region having a duration of from 2 to 20 milliseconds, such train of electrical pulses being applied to the patient through probes placed on the skin of the patient in the region of the pain or in pre-determined regions of sedation-induction. The pulse waveform taught by this invention approaches that of the H-reflex in humans.

BRIEF DESCRIPTION OF THE DRAWINGS

The natue of the present invention can best be understood from the description set forth hereinafter taken in conjunction with the accompanying drawings, in which.

DETAILED DESCRIPTION OF THE PREFERRED EMBODIMENT

Figure 1:
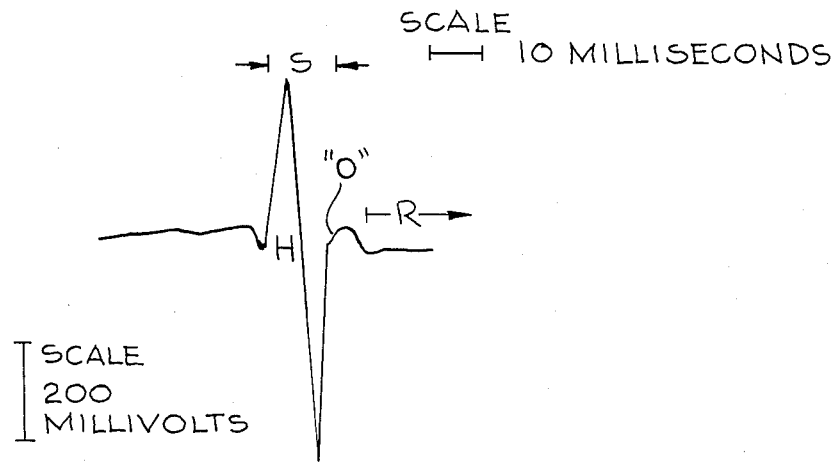
FIG. 1 is a graphical representation of an H-reflex waveform in a human being; and, FIG. 2 is a schematic diagram of a circuit, according to the present invention, which produces a waveform which simulates the H-reflex waveform of FIG. 1.

In FIG. 1, the character of an H-reflex muscle-response voltage in a human being is presented.

The H-reflex, a post-synaptic reflex, was first discovered in 1918. This reflex is not present in most normal muscles or at least can not be elicited by stimulation of an appropriate peripheral nerve after the age of one year. From birth until approximately the first birthday, the reflex is gradually "suppressed" in almost all muscles, except those innervated by the S1 root and the tibial nerve. The H-reflex is elicitable in virtually any muscle of a person who has a central nervous system lesion at or below the midbrain stem. Such a lesion at this level seemingly releases the inhibition of the H-reflex which is normally present in adults. An easily elicitable H-reflex occurs in a complete spinal cord quadraplegic by stimulation of almost any mixed nerve below the lesion. The textbook shape of the H-reflex, as presented in FIG. 1, is a positive triangular pulse immediately followed by a negative triangular pulse. Such a waveform resembles the RS segments of a normal electrocardiogram.

When the physician—co-inventor of this invention was working on patients with waveform generators that each produced a single triangular pulse train, he found that if he placed two separate waveform generators into use, so that one would induce a positive triangular pulse train transcutaneously while the other would induce a negative triangular pulse train through the skin of the same patient, such a combination TENS device would produce better pain relief than either generator by itself.

The positive and negative-going pulses are seen to be triangular in shape with a total duration approximating 10 milliseconds and a peak-to-peak amplitude of about 800 millivolts for normal stimulation. The stimulation period "S" of high amplitude is seen to be followed by a rest period "R" within the muscle. The duration of the rest period "R" is at least one half as long as the stimulation period "S".

Following or preceding the H-reflex stimulation period "S" there may be a portion of the "off" region "O" which is displaced from zero.

The inventors herein have hypothesized and proved that if a TENS wavetrain which simulates the H-reflex wavetrain is applied to a human being through probes topically positioned, optimum therapeutic results occur.

Figure 2:
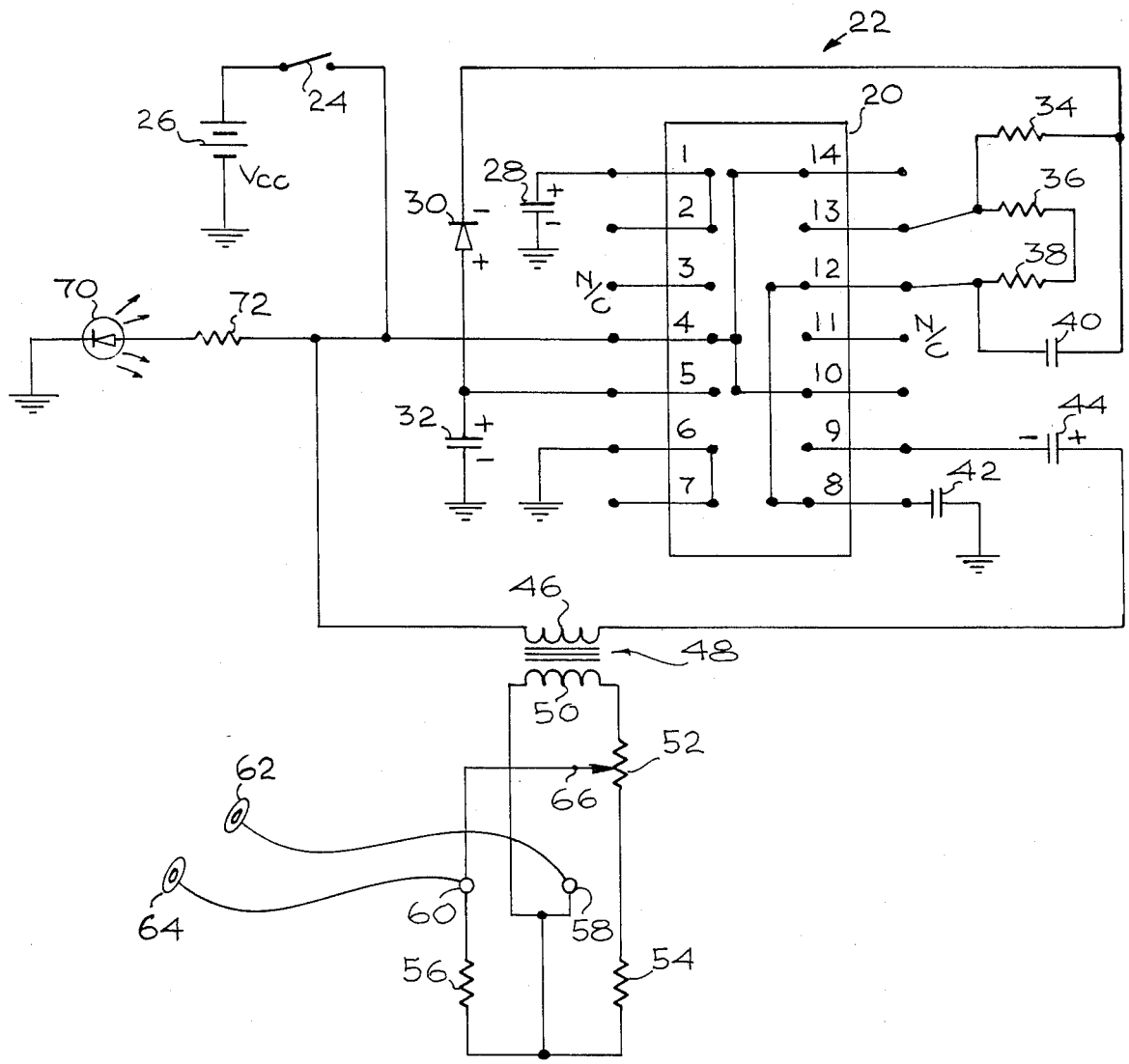

One circuit which produces such a TENS wavetrain is shown in FIG. 2. In FIG. 2, integrated circuit chip 29 is at the heart of TENS unit 22. Chip 20 is a dual timer chip such as type NE 556N which is available from Texas Instruments Co., and elsewhere. When switch 24 is closed, a d.c. voltage (Vcc) is provided from battery 26 to pin 4 of chip 20. Battery 26 may be replaced by an a.c. to d.c. adaptor (not shown). Pin 6 of chip 20 is tied to ground so pin 5 is set high enabling pins 1 and 2 and causing capacitor 28 to commence charging exponentially towards ⅔ Vcc. When capacitor 28 reaches ⅔ Vcc the threshold comparator internal to chip 20 resets its flip-flop causing capacitor 28 to discharge, thus returning the digital output at pin 5 to the low or "zero" state. When the input voltage to the trigger comparator internal to chip 20 falls below ⅓ Vcc the comparator output triggers the flip-flop so that its output goes low. This turns off the transistor in chip 20 which is discharging capacitor 28 and causes pin 5 to return to a "one" or high state. The time constant of this cycle is determined by capacitor 28 and the internal resistance of the associated circuit chip 20. This is the monostable portion of chip 20.

Pins 8 thru 13 of chip 20 comprise the connections to the a-stable portion of the dual timer chip 20. Diode 30 passes to pin 13 only the positive portion of the voltage waveform appearing at pin 5. Capacitor 32 further cuts off any negative-going signal appearing at pin 5. A free-running oscillator exists on the a-stable side of chip 20. The resistors 34, 36 and 38 in combination with capacitor 40 set the frequency of that oscillation. Capacitor 42 holds pin 12 just above ground potential.

Both reset pins 4 and 10 are tied to Vcc. The reset pins are provided to permit discharging a timing capacitor, such as capacitor 40, thus interrupting the timing cycle. As long as a reset pin is low, the transistor for discharging capacitor 40 is turned "on" and prevents capacitor 40 from charging. If the reset voltage is applied, in the conventional circuit, the digital output condition will remain the same. To prevent this phenomenon the reset pins are tied to Vcc.

There appears at pin 9 substantially a square wave with a frequency given by the formula:

$$f = \frac{1}{T} = \frac{1.44}{[R_{34} + 2(R_{36} + R_{38})] \cdot C_{40}}$$

If, purely by way of example,
$R_{34} = 390K$ ohms
$R_{36} = 22K$ ohms
$R_{38} = 56K$ ohms, and
$C_{40} = 0.1$ uf; then,
the frequency of oscillation of the substantially square wave is 26.3736 Hz. However, as has been noted by these inventors, square waves do not have the optimal therapeutic effect achieved by these inventions. Therefore wave shaping is necessary to approach as closely as possible the H-reflex waveshape of FIG. 1. It should be noted that an M response or motor neuron response is closely akin to the H-reflex waveform but of possibly different duration and of a different number of half cycles.

Wave shaping is achieved by a combination of capacitor 44 and the inductance of primary 46 in transformer 48. Transformer 48 serves two functions, therefore, first, to help shape the wave from pin 9 so that it closely approaches the H-reflex wave-shape and, second, to multiply the potential of that wave. The step-up ratio is approximately 20 to 1. The potential appearing across secondary 50 is applied across intensity control 52 through a resistor 54. Resistor 56 acts as an isolating resistor.

Output signals from generator 22 are taken from terminals 58, 60 and are fed to a pair of electrodes 62, 64. Electrodes 62, 64 have therein pads which may be moistened to give reasonable electrical conduction when they are applied to the skin of a patient. The potential level of the signals applied may reach 150 volts peak-to-peak but the transcutaneous current is low. By using the bi-polar triangularly-shaped waves (simulating the H-reflex wave) taught by this invention the effectiveness of this TENS unit is increased and the amplitude of the applied wavetrain may be reduced as well as the time during which the wavetrain is applied. Battery consumption is, thus, decreased.

The intensity of the TENS signal applied to electrodes 62, 64 can be adjusted by moving the position of arm 66 of potentiometer 52.

Unit operation is indicated by LED 70 which is coupled through resistor 72 to the high side of power source 26 when switch 24 is closed.

It should be understood that this invention is not limited to the circuit of FIG. 2. That circuit, or other circuits which are capable of generating the bi-polar, triangular type wave or, more specifically, the electronically simulated H-reflex wave taught by this invention, are intended to be covered by the appended claims.

What is claimed is:
1. A process for controlling pain which comprises:
  (a) attaching electrodes for transcutaneous current flow to a patient suffering pain at an area in which said patient is suffering pain;
  (b) generating a uniform train of discrete triangular electrical impulses which simulate the characteristic H-reflex pulse train, each of said impulses having a positive triangular component and a contiguous negative triangular component at a frequency within the range of approximately 2 to 20 impulses per second successive ones of said impulses being separated by a rest period within the range of 10 to 15 milliseconds, said rest period being of substantially constant amplitude and corresponding to said characteristic H-reflex pulse train, with the time duration of the rest period being at least one-half of the time duration of said combined time period;
  (c) conducting said uniform train of discrete triangular electrical impulses to said electrodes and thereby to said area for transcutaneous current flow for a therapy period thereby ameliorating said patient by relieving said pain.

* * * * *

UNITED STATES PATENT AND TRADEMARK OFFICE
CERTIFICATE OF CORRECTION

PATENT NO. : 4,723,552

DATED : 02/09/88

INVENTOR(S) : Kenyon et al.

It is certified that error appears in the above-identified patent and that said Letters Patent is hereby corrected as shown below:

| COLUMN | LINE | DESCRIPTION |
|--------|------|-------------|
| 01 | 63 | delete "natue" insert --nature-- |

Signed and Sealed this

Sixth Day of December, 1988

Attest:

DONALD J. QUIGG

Attesting Officer

Commissioner of Patents and Trademarks